(12) United States Patent
Nishioka et al.

(10) Patent No.: US 12,070,296 B2
(45) Date of Patent: Aug. 27, 2024

(54) CUFF UNIT AND SPHYGMOMANOMETER

(71) Applicants: OMRON HEALTHCARE CO., LTD., Muko (JP); THE UNIVERSITY OF SHIGA PREFECTURE, Hikone (JP); OMRON CORPORATION, Kyoto (JP)

(72) Inventors: Yasutaka Nishioka, Shiga (JP); Kenta Azuma, Shiga (JP); Minoru Taniguchi, Kyoto (JP); Chisato Tawara, Kyoto (JP); Tsuyoshi Hamaguchi, Otsu (JP)

(73) Assignees: OMRON HEALTHCARE CO., LTD., Muko (JP); THE UNIVERSITY OF SHIGA PREFECTURE, Hikone (JP); OMRON CORPORATION, Kyoto (JP)

( * ) Notice: Subject to any disclaimer, the term of this patent is extended or adjusted under 35 U.S.C. 154(b) by 909 days.

(21) Appl. No.: 17/023,148

(22) Filed: Sep. 16, 2020

(65) Prior Publication Data

US 2020/0405162 A1    Dec. 31, 2020

Related U.S. Application Data

(63) Continuation of application No. PCT/JP2019/007449, filed on Feb. 27, 2019.

(30) Foreign Application Priority Data

Mar. 30, 2018   (JP) ................................. 2018-067427

(51) Int. Cl.
*A61B 5/022*    (2006.01)

(52) U.S. Cl.
CPC ...... *A61B 5/02233* (2013.01); *A61B 5/02225* (2013.01); *A61B 2560/04* (2013.01); *A61B 2562/0247* (2013.01)

(58) Field of Classification Search
CPC ............ A61B 5/02233; A61B 5/02225; A61B 2560/04; A61B 2562/0247
See application file for complete search history.

(56) References Cited

U.S. PATENT DOCUMENTS

| | | | |
|---|---|---|---|
| 2013/0046191 A1* | 2/2013 | Lin ..................... | A61B 5/02233 600/500 |
| 2019/0133215 A1* | 5/2019 | Whalen ................ | A61B 17/135 |

FOREIGN PATENT DOCUMENTS

| | | |
|---|---|---|
| JP | H11-318835 A | 11/1999 |
| JP | 2013-043084 A | 3/2013 |

(Continued)

OTHER PUBLICATIONS

Oct. 7, 2019 International Preliminary Report on Patentability issued in International Patent Application No. PCT/JP2019/007449.

(Continued)

*Primary Examiner* — Devin B Henson
*Assistant Examiner* — Evelyn Grace Park
(74) *Attorney, Agent, or Firm* — Oliff PLC

(57) ABSTRACT

A cuff unit of the present invention includes a first wall and a second wall that face each other with an object which has a rod shape interposed therebetween, an actuator that is capable of moving the first wall and the second wall in parallel with each other in a direction in which the first wall and the second wall relatively approach each other or separate from each other, a pressing fluid bag that is provided on a surface of the first wall on a side facing the object and that receives supply of a fluid from outside to inflate and press the object, and a restraining fluid bag that is provided on a surface of the second wall on a side facing the object and that receives supply of a fluid from outside to inflate along the periphery of the object.

5 Claims, 13 Drawing Sheets

(56) References Cited

FOREIGN PATENT DOCUMENTS

| JP | 2016-158805 A | 9/2016 |
| JP | 2017-093991 A | 6/2017 |
| WO | 2017/094276 A1 | 6/2017 |

OTHER PUBLICATIONS

May 28, 2019 International Search Report Issued in International Patent Application No. PCT/JP2019/007449.

* cited by examiner

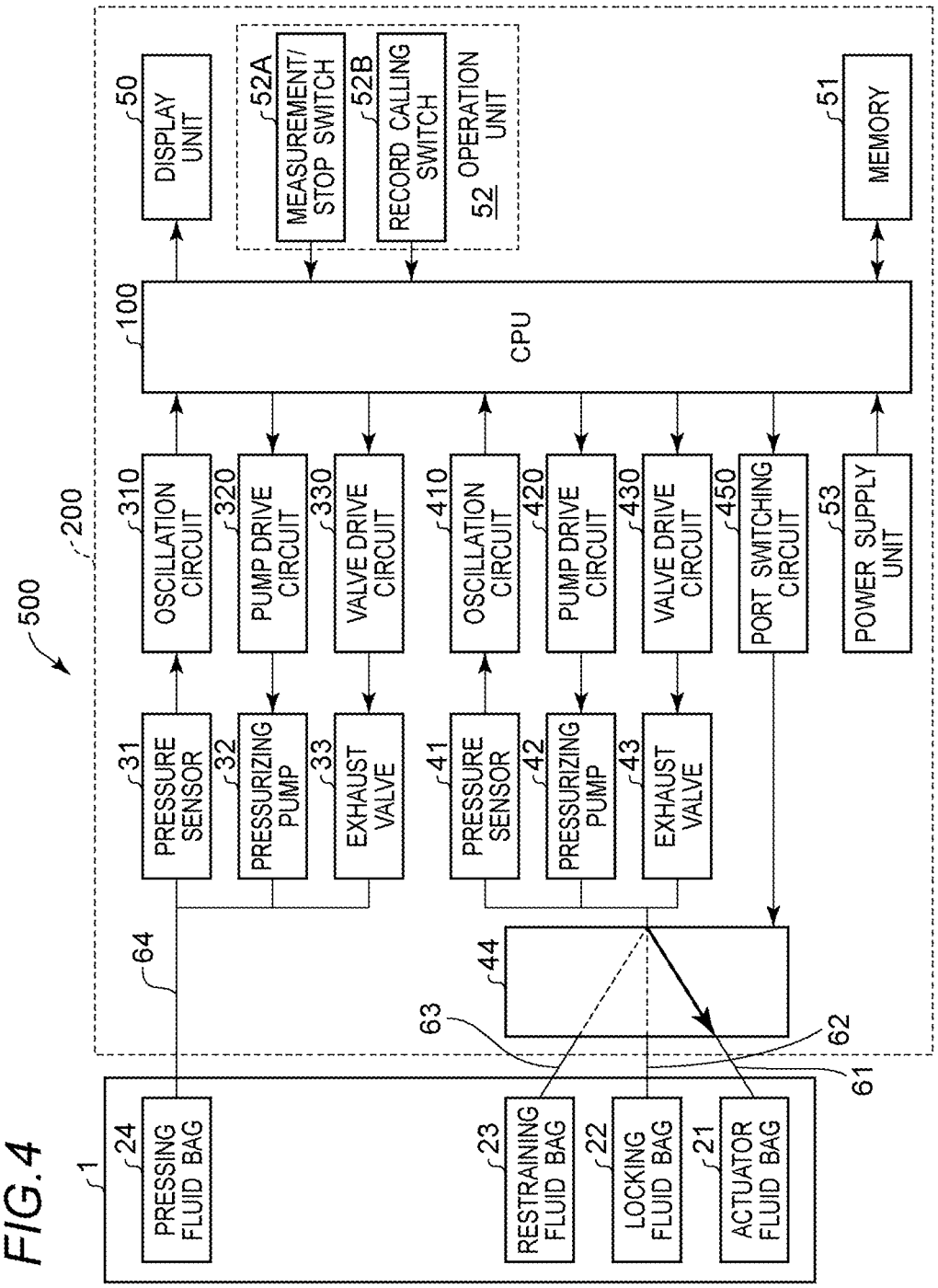

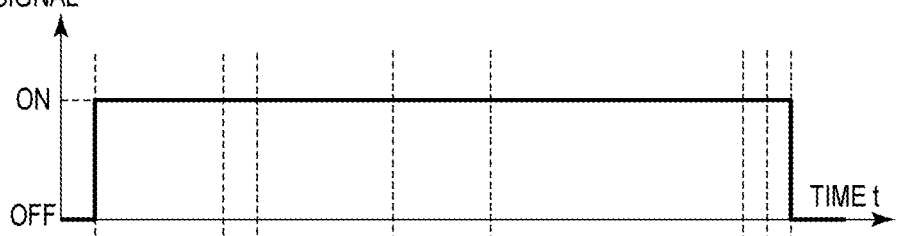
FIG.5A
P1 ON/OFF SIGNAL
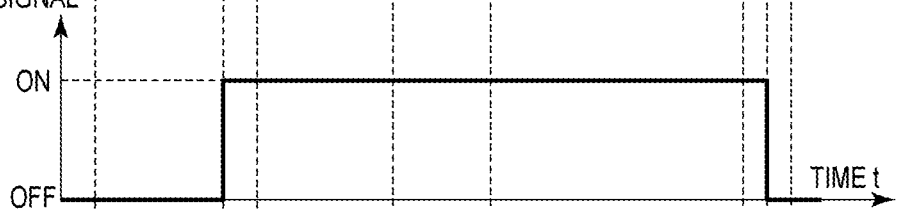
FIG.5B
P2 ON/OFF SIGNAL
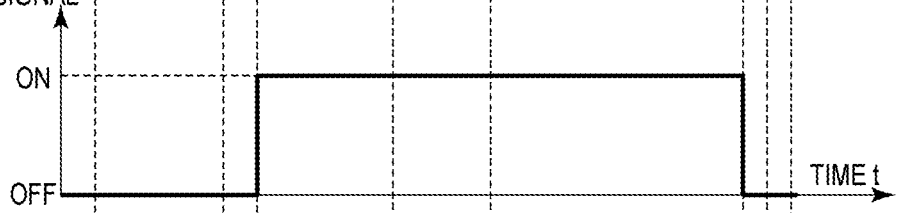
FIG.5C
P3 ON/OFF SIGNAL
FIG.5D
PRESSURE P4
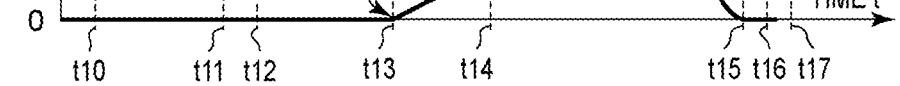

WHEN t = t10

WHEN t = t11

WHEN t = t12

WHEN t = t14

WHEN t = t15

WHEN t = t16

WHEN t = t17

CUFF UNIT AND SPHYGMOMANOMETER

CROSS-REFERENCE TO RELATED APPLICATION

This is a continuation application of International Application No. PCT/JP2019/007449, with an International filing date of Feb. 27, 2019, which claims priority of Japanese Patent Application No. 2018-067427 filed on Mar. 30, 2018, the entire content of which is hereby incorporated by reference.

TECHNICAL FIELD

The present invention relates to a cuff unit, and more particularly to a slide-type cuff unit that automatically restrains and presses an object by using a slide mechanism. The present invention also relates to a sphygmomanometer including such a cuff unit.

BACKGROUND ART

Conventionally, as such a cuff unit, for example, a cuff unit as disclosed in WO 2017/094276 A is known. The cuff unit includes an actuator that receives supply of a fluid and deforms, and is automatically wound around an object (a portion to be measured such as an arm) sequentially from a base portion of the actuator toward the front-end side while adapting to the thickness of the object to grip the object.

SUMMARY OF THE INVENTION

However, in the cuff unit described in Patent Document 1 (WO 2017/094276 A), there is a problem that the restraining force and the pressing force are insufficient as a cuff unit because the operation range of the actuator is large and the gap between the actuator and an object becomes large when the object is gripped.

Therefore, an object of the present invention is to provide a cuff unit having a sufficiently great restraining force and pressing force as a cuff unit. Moreover, an object of the present invention is to provide a sphygmomanometer including such a cuff unit.

Means for Solving the Problems

In order to solve the above-mentioned problem, a cuff unit restraining and pressing an object which has a rod shape, the cuff unit of the present disclosure comprises:

a first wall and a second wall that face each other with the object which has the rod shape interposed therebetween;

an actuator that is capable of moving the first wall and the second wall in parallel with each other in a direction in which the first wall and the second wall relatively approach each other or separate from each other;

a pressing fluid bag that is provided on a surface of the first wall on a side facing the object and that receives supply of a fluid from outside to inflate and press the object;

a restraining fluid bag that is provided on a surface of the second wall on a side facing the object and that receives supply of a fluid from outside to inflate along a periphery of the object;

a third wall that is disposed to face a surface of the second wall on a side opposite to the first wall;

a support wall that integrally connects sides of the first wall and the third wall which face each other; and an actuator fluid bag that is provided between the second wall and the third wall and that receives supply of a fluid from outside to expand, wherein the actuator expands or contracts the actuator fluid bag when the actuator moves the first wall and the second wall in parallel with each other in the direction in which the first wall and the second wall relatively approach each other or separate from each other.

In the present description, the term "object which has a rod shape" typically refers to a portion to be measured such as an upper limb (wrist, upper arm, or the like) or a lower limb (ankle or the like); however, is not limited to part of a living body. The object may also be an inanimate object.

In addition, the term "outside" in the phrase, a pressing fluid bag "receives supply of a fluid from outside", means outside of the pressing fluid bag. Similarly, the term "outside" in the phrase, a restraining fluid bag "receives supply of a fluid from outside", means outside of the restraining fluid bag. Similarly, the term "outside" in the phrase, an actuator fluid bag to be described later "receives supply of a fluid from outside", means outside of the actuator fluid bag.

In another aspect, a sphygmomanometer of the present disclosure comprises:

the cuff unit; and a pressure sensor that detects pressure of the pressing fluid bag.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 4 is a diagram illustrating a block configuration of a sphygmomanometer of one embodiment including the cuff unit.

FIG. 5A is a diagram illustrating a P1 on/off signal indicating a period in which the actuator fluid bag illustrated in FIG. 1 should be pressurized. FIG. 5B is a diagram illustrating a P2 on/off signal indicating a period in which the locking fluid bag illustrated in FIG. 1 should be pressurized. FIG. 5C is a diagram illustrating a P3 on/off signal indicating a period in which the restraining fluid bag illustrated in FIG. 1 should be pressurized. FIG. 5D is a diagram illustrating a change in pressure P4 applied to the pressing fluid bag illustrated in FIG. 1 with the passage of time t.

DESCRIPTION OF EMBODIMENTS

Hereinafter, an embodiment of the present invention will be described in detail with reference to the drawings.

(Configuration of Cuff Unit)

Figure 1:
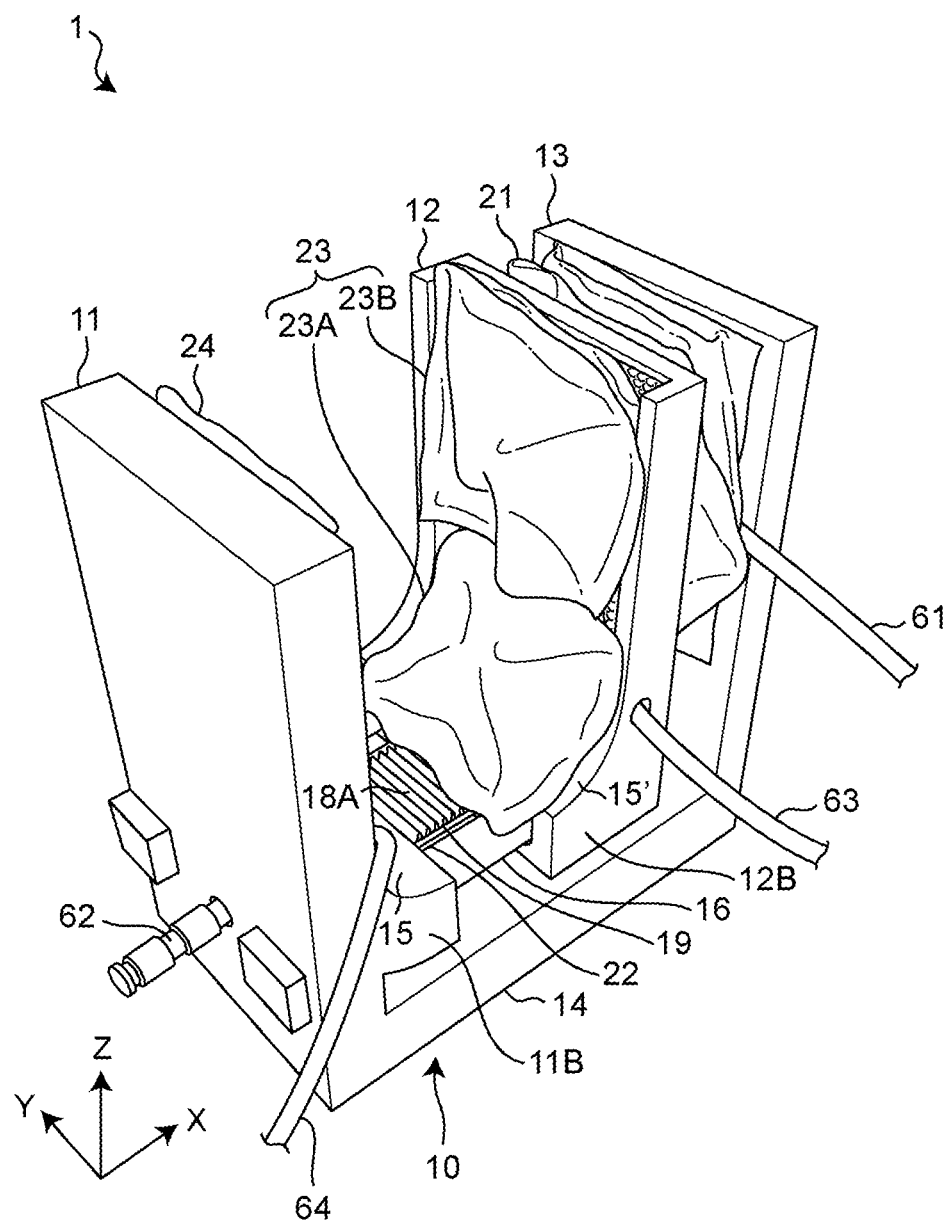
FIG. 1 is a perspective view illustrating an external appearance of a cuff unit (in an open state) according to an embodiment of the present invention.

FIG. 1 is a perspective view illustrating an external appearance of a cuff unit (in an open state) 1 according to an embodiment of the present disclosure. For easy understanding, an XYZ Cartesian coordinate system is also illustrated in the drawings as appropriate. Furthermore, FIG. 2A illustrates the cuff unit 1 as viewed from above (+Z direction) in FIG. 1, and FIG. 3 illustrates the cuff unit 1 as viewed from the right side (−Y direction) in FIG. 1.

Figure 2A:
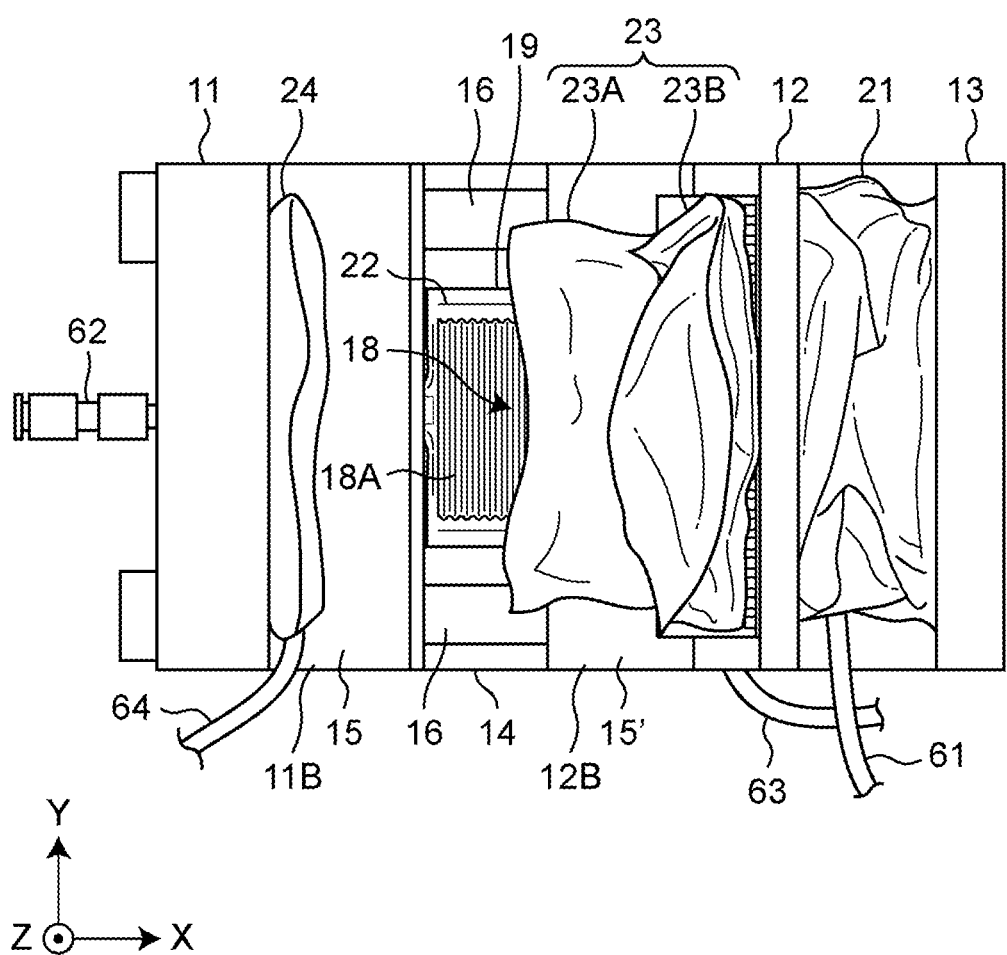
FIG. 2A is a view illustrating the cuff unit as viewed from above in FIG. 1.
Figure 3:
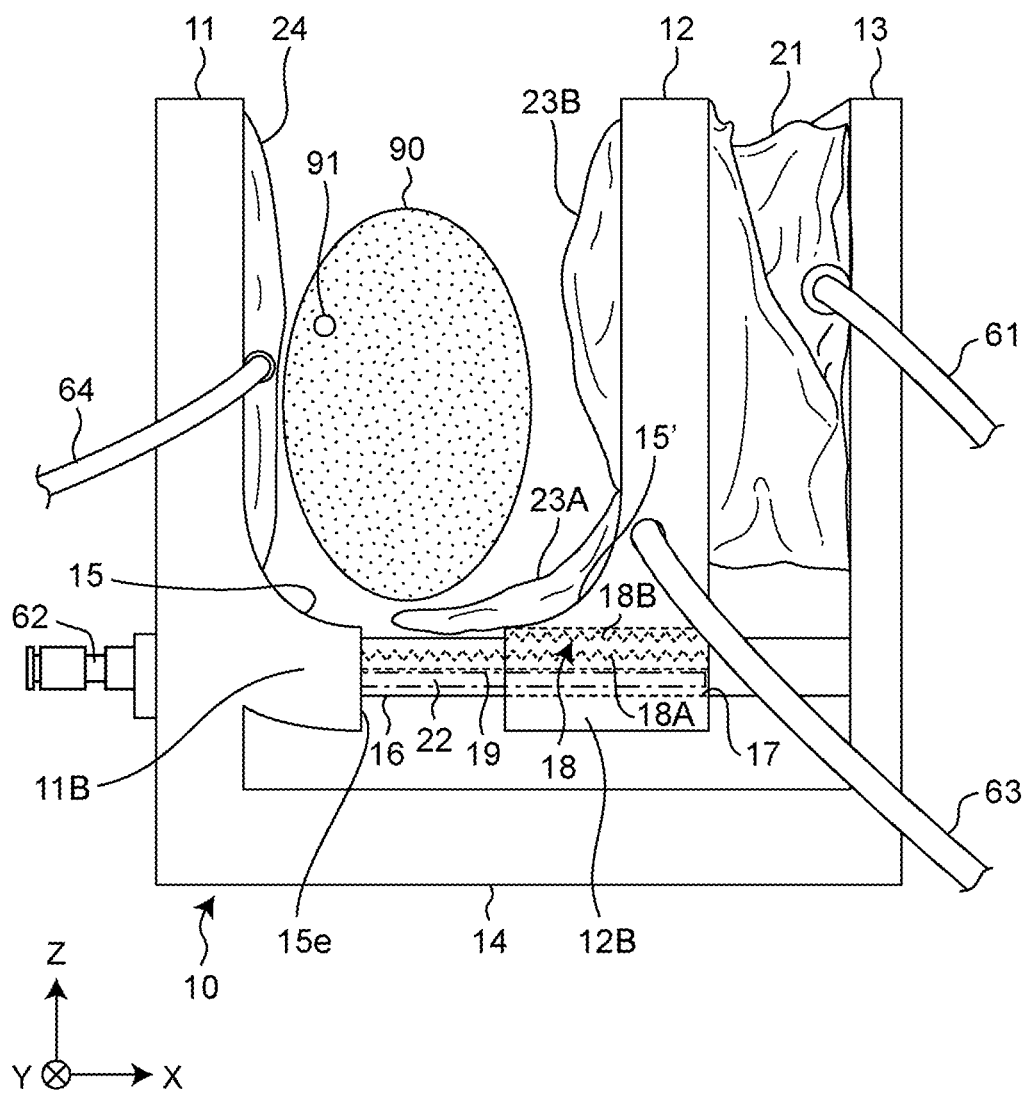
FIG. 3 is a view illustrating the cuff unit as viewed from the right side in FIG. 1.

As can be seen from FIGS. 1, 2A, and 3, the cuff unit 1 includes a first wall 11 having a substantially rectangular flat plate shape, a second wall 12 having a substantially rectangular flat plate shape and provided so as to face the first wall, a third wall 13 having a substantially rectangular flat plate shape and provided so as to face a side of the second wall 12 opposite to the first wall 11, a support wall 14 integrally connecting the lower sides of the first wall 11 and the third wall 13 facing each other, an actuator fluid bag 21, a locking fluid bag 22, a restraining fluid bag 23, and a pressing (measuring) fluid bag 24. In this example, the cuff unit 1 is designed to restrain and press a wrist 90 (see FIG. 3) which is an object having a rod shape in order to measure blood pressure.

The first wall 11, the third wall 13, and the support wall 14 constitute an integral outer frame 10 having a substantially U shape. The first wall 11 includes a first leg portion 11B which is provided as part of the first wall 11 in a lower portion thereof slightly separated from the support wall 14. The first leg portion 11B is branched, and protrudes toward the second wall 12. The upper surface of the first leg portion 11B is a receiving portion 15 that is curved so as to surround the wrist 90.

The second wall 12 includes a second leg portion 12B which is provided in a lower portion of the second wall 12. The second leg portion 12B protrudes toward the first leg portion 11B of the first wall 11. The upper surface of the second leg portion 12B is a receiving portion 15' that is curved so as to surround the wrist 90. As can be seen from FIG. 2B (state in which the actuator fluid bag 21, the restraining fluid bag 23, and the pressing fluid bag 24 are omitted in FIG. 2A), through holes 12u, 12v are formed in portions of the second leg portion 12B corresponding to both sides in the Y direction. Each of the through holes 12u, 12v has a circular cross section, extends in the X direction, and penetrates the second leg portion 12B. These through holes 12u, 12v are provided for passing rod members 16, 16 to be described later therethrough. Furthermore, a through hole 17 is formed in a portion of the second leg portion 12B corresponding to the center in the Y direction. The through hole 17 has a circular cross section, extends in the X direction, and penetrates the second leg portion 12B. The through hole 17 is provided so as to configure a lock mechanism to be described later.

Two rod members 16, 16 each having a circular cross section are laid across the first wall 11 and the third wall 13, from a front end 15e of the receiving portion 15 of the first wall 11 through the through holes 12u, 12v of the second wall 12 in the direction perpendicular to the first wall 11. In this example, the rod members 16, 16 are fitted in the through holes 12u, 12v of the second leg portion 12B in parallel with each other and extend in the X direction between the first wall 11 and the third wall 13. These rod members 16, 16 stably support the second wall 12 and function as a guide for moving the second wall 12 in parallel in the X direction between the first wall 11 and the third wall 13.

As can be seen from FIGS. 2B and 3, on the upper surface as an edge portion of the through hole 17 having a rectangular cross section in the second wall 12, an uneven first engaging portion 18B forming part of a lock mechanism 18 to be described later is formed.

The third wall 13 is disposed along the back surface side (surface on the side opposite to the first wall 11) of the second wall 12, and enables parallel movement operation of the second wall 12 together with the actuator fluid bag 21 to be described later.

The actuator fluid bag 21 is disposed between the surface of the third wall 13 facing the second wall 12 and the surface of the second wall 12 facing the third wall 13. In this example, the actuator fluid bag 21 is attached to the surface of the third wall 13 facing the second wall 12 and the surface of the second wall 12 facing the third wall 13 by bonding. A flexible tube 61 for supplying and exhausting air as a fluid is attached to the actuator fluid bag 21. The actuator fluid bag 21 expands by being supplied with air from a pressurizing pump 42 in FIG. 4 to be described later, through a 3-port valve 44 and a flexible tube 61, and moves the first wall 11 and the second wall 12 in parallel with each other in a direction in which the first wall 11 and the second wall 12 relatively approach each other along the rod members 16. Furthermore, air is discharged through an exhaust valve 43 from the actuator fluid bag 21 and the actuator fluid bag 21 contracts to allow the first wall 11 and the second wall 12 to move in parallel with each other in the direction in which the first wall 11 and the second wall 12 are relatively separated from each other.

The restraining fluid bag 23 is divided into two parts, that is, an upper portion 23A and a lower portion 23B, provided on the surface of the second wall 12 facing the first wall 11. In this example, the upper portion 23A and the lower portion 23B of the restraining fluid bag 23 are attached to the surface of the second wall 12 facing the first wall 11, by bonding. A flexible tube 63 for supplying and exhausting air as a fluid is attached to the upper portion 23A and the lower portion 23B of the restraining fluid bag 23. Air is supplied from the pressurizing pump 42 through the 3-port valve 44 and the flexible tube 63 to the upper portion 23A and the lower portion 23B of the restraining fluid bag 23 simultaneously, and the upper portion 23A and the lower portion 23B expand along the periphery of the wrist 90. Air is discharged from the upper portion 23A and the lower portion 23B simultaneously through the exhaust valve 43, and the upper portion 23A and the lower portion 23B contract.

The pressing (measuring) fluid bag 24 is disposed on the surface of the first wall 11 facing the second wall 12. In this example, the pressing fluid bag 24 is attached to the surface of the first wall 11 facing the second wall 12, by bonding. A flexible tube 64 for supplying and exhausting air as a fluid is attached to the pressing fluid bag 24. Air is supplied from the pressurizing pump 42 through the 3-port valve 44 and the flexible tube 64, and the pressing fluid bag 24 expands so as to press the wrist 90. Air is discharged from the exhaust valve 43, and the pressing fluid bag 24 contracts. Furthermore, the pressing fluid bag 24 is used when the pressure of the pressing fluid bag 24 is detected by a pressure sensor 31 in FIG. 4 to be described later, and a change the arterial volume generated in an artery 91 of the wrist 90 (see FIG. 3) is extracted as a pulse wave signal to calculate the blood pressure value.

In this example, the wrist 90 is provided between the first wall 11 and the second wall 12, and the first wall 11 and the second wall 12 face each other with the wrist 90 interposed therebetween. The actuator fluid bag 21 receives supply of a fluid to inflate, and moves the first wall 11 and the second wall 12 to in parallel with each other in the direction in which the first wall 11 and the second wall 12 relatively approach each other. The restraining fluid bag 23 receives supply of a fluid to inflate, and extends along the periphery of the wrist 90 from the surface of the second wall 12 on the side facing the wrist 90. The pressing fluid bag 24 receives supply of a fluid from outside to inflate, and presses the wrist 90 from the surface of the first wall 11 on the side facing the wrist 90. Here, since the first wall 11 and the second wall 12 relatively approach each other with the wrist 90 interposed therebetween, the restraining fluid bag 23 inflates in a relatively narrow range between the second wall 12 and the wrist 90. Further, the pressing fluid bag 24 inflates in a relatively narrow range between the first wall 11 and the wrist 90. Therefore, restraining force and pressing force can be made sufficiently great as the cuff unit 1. Note that when the wrist 90 is removed from the cuff unit 1, air is discharged from the pressing fluid bag 24 and the restraining fluid bag 23, and the actuator fluid bag 21 moves the first wall 11 and the second wall 12 in parallel with each other in the direction in which the first wall 11 and the second wall 12 relatively separate from each other. As a result, it is possible to remove the wrist 90 from the cuff unit 1.

Figure 2B:
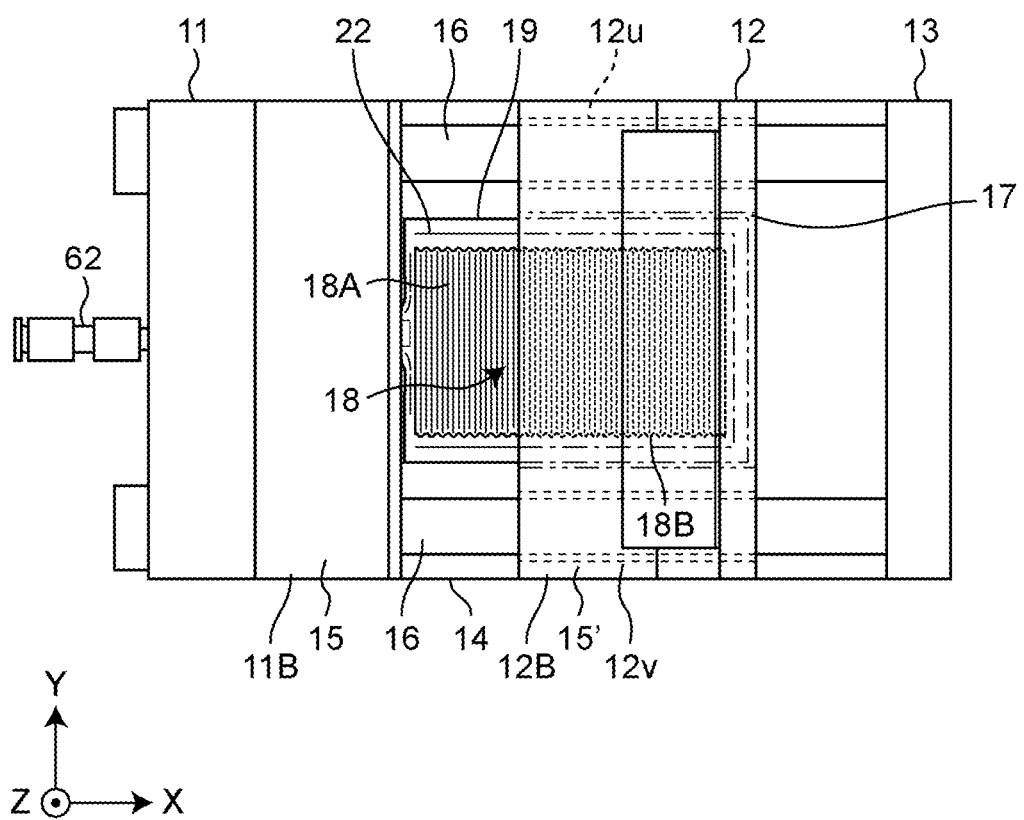
FIG. 2B is a view illustrating a state in which an actuator fluid bag, a restraining fluid bag, and a pressing fluid bag are omitted in the cuff unit in FIG. 2A.

As can be seen from FIGS. 2B and 3, in this example, the lock mechanism 18 includes the above-described uneven first engaging portion 18B formed on the upper surface of the through hole 17 of the second wall 12, the plate member 19 disposed so as to the upper surface of the through hole 17 of the second wall 12, and the locking fluid bag 22. As can be seen from FIG. 2B, in this example, each of the plate member 19 and the locking fluid bag 22 has a rectangular planar shape (on the XY plane), extends over the range where the second leg portion 12B moves in the direction (X direction) in which the second wall 12 moves in parallel, and is disposed so as to be fixed to the first wall 11. On the upper surface (surface facing the first engaging portion 18B) of the plate member 19, an uneven second engaging portion 18A is provided. A flexible tube 62 for supplying and exhausting air is attached to the locking fluid bag 22. The flexible tube 62 penetrates the first leg portion 11B of the first wall 11 in the X direction. If the locking fluid bag 22 receives supply of air from the pressurizing pump 42 in FIG. 4 to be described later through the 3-port valve 44 and the flexible tube 62 to expand, the locking fluid bag 22 urges the plate member 19 toward the upper surface of the through hole 17 of the second wall 12. Therefore, the second engaging portion 18A meshes with the first engaging portion 18B. As a result, regarding the direction (X direction) in which the second wall 12 moves in parallel, the second wall 12 is locked with respect to the first wall 11.

When the wrist 90 is removed from the cuff unit 1, air is discharged from the locking fluid bag 22, and then the first engaging portion 18B and the second engaging portion 18A are disengaged. As a result, it is possible to remove the wrist 90 from the cuff unit 1.

In this example, the lock mechanism 18 can fix the relative position of the second wall 12 with respect to the first wall 11 regarding the direction (X direction) in which the second wall 12 moves in parallel. Therefore, the restraining force and the pressing force can be made greater as the cuff unit 1. In addition, when the user feels an abnormality during use by any chance, it is possible to easily remove the wrist 90 from the cuff unit 1 by deforming the locking fluid bag 22, the pressing fluid bag 24, and the actuator fluid bag 21.

In this example, expansion or contraction of the actuator fluid bag 21 and the locking fluid bag 22 can be performed according to control similar to control of expansion or contraction of the restraining fluid bag 23 and the pressing fluid bag 24. Therefore, the control system of this cuff unit 1 is simplified.

(Block Configuration of Sphygmomanometer)

FIG. 4 illustrates a schematic block configuration of a sphygmomanometer 500. A main body 200 of the sphygmomanometer 500 incorporates, in addition to a display unit 50 and an operation unit 52, a CPU (Central Processing Unit) 100 serving as a control unit, a memory 51 serving as a storage unit, a power supply unit 53, a pressurizing pump 32, an exhaust valve 33, and a pressure sensor 31, as elements for blood pressure measurement. Furthermore, the main body 200 incorporates an oscillation circuit 310 that converts output from the pressure sensor 31 into a frequency, a pump drive circuit 320 that drives the pressurizing pump 32, and a valve drive circuit 330 that drives the exhaust valve 33. Moreover, the main body 200 incorporates a pressure sensor 41, the pressurizing pump 42, the exhaust valve 43, and the 3-port valve 44 as elements for driving the cuff unit. Furthermore, the main body 200 incorporates an oscillation circuit 410 that detects output from the pressure sensor 41, a pump drive circuit 420 that drives the pressurizing pump 42, a valve drive circuit 430 that drives an exhaust valve 43, and a port switching circuit 450 that drives the 3-port valve 44 to switch the port.

The display unit 50 includes a display, an indicator, and the like, and displays predetermined information according to a control signal from the CPU 100.

A measurement/stop switch 52A and a record calling switch 52B included in the operation unit 52 transmit operation signals to the CPU 100 according to an instruction from the user.

The memory 51 stores data of a program for controlling the sphygmomanometer 500, data used for controlling the sphygmomanometer 500, setting data for setting various functions of the sphygmomanometer 500, data of a measurement result of a blood pressure value, and the like. In addition, the memory 51 is used as a working memory or the like when the program is executed.

According to the program for controlling the sphygmomanometer 500 stored in the memory 51, in response to an operation signal from the operation unit 52, the CPU 100 performs control for driving the pressurizing pumps 32, 42, the exhaust valves 33, 43, and the 3-port valve 44, on the basis of signals from the pressure sensors 31, 41. The drive sequences will be described in detail with reference to FIG. 5. In particular, the CPU 100 calculates the blood pressure value on the basis of the signal from the pressure sensor 31, and controls the display unit 50 and the memory 51.

The power supply unit 53 supplies power to each of the CPU 100, the pressure sensors 31, 41, the pressurizing pumps 32, 42, the exhaust valves 33, 43, the display unit 50, the memory 51, the oscillation circuits 310, 410, the pump drive circuits 320, 420, the valve drive circuits 330, 430, and the 3-port valve 44.

The pressurizing pump 32 supplies air to the pressing fluid bag 24 through the flexible tube 64 in order to increase the pressure (hereinafter appropriately referred to as "cuff pressure") in the pressing fluid bag 24 attached to the cuff unit 1. The exhaust valve 33 is opened and closed to discharge or enclose air in the pressing fluid bag 24 to control the cuff pressure. Similarly, in order to increase the pressure in the actuator fluid bag 21, the locking fluid bag 22, and the restraining fluid bag 23 attached to the cuff unit 1, the pressurizing pump 42 supplies air to the respective fluid bags through the 3-port valve 44 and the flexible tubes 61, 62, 63. The exhaust valve 43 is opened and closed to discharge or enclose the air in the actuator fluid bag 21, the locking fluid bag 22, and the restraining fluid bag 23.

The pump drive circuits 320, 420 drive the pressurizing pumps 32, 42, respectively, according to a control signal transmitted from the CPU 100. The valve drive circuits 330, 430 open and close the exhaust valves 33, 43, respectively, on the basis of a control signal transmitted from the CPU 100. The port switching circuit 450 switches the 3-port valve 44 to switch the flow path through which air is supplied to or discharged from any one of the actuator fluid bag 21, the locking fluid bag 22, and the restraining fluid bag 23, on the basis of a control signal transmitted from the CPU 100. Furthermore, the port valves other than the one port that has been switched are closed, and air supplied to the fluid bags whose port valves are closed is trapped therein.

The pressure sensor 31 and the oscillation circuit 310 function as a pressure detection unit that detects the pressure of the pressing fluid bag 24. The pressure sensor 31 is, for example, a piezoresistive pressure sensor, and is connected through the flexible tube 64 to the pressurizing pump 32, the exhaust valve 33, and the pressing fluid bag 24 attached to the cuff unit 1. In this example, the oscillation circuit 310 oscillates on the basis of an electric signal value based on a change in electric resistance due to the piezoresistive effect from the pressure sensor 31, and outputs a frequency signal having a frequency corresponding to the electric signal value of the pressure sensor 31 to the CPU 100.

Similarly, the pressure sensor 41 and the oscillation circuit 410 function as a pressure detection unit that detects the pressure of any one of the actuator fluid bag 21, the locking fluid bag 22, and the restraining fluid bag 23. The pressure sensor 41 is, for example, a piezoresistive pressure sensor, and is connected through the 3-port valve 44 and the flexible tubes 61, 62, 63 to the pressurizing pump 42, the exhaust valve 43, and the actuator fluid bag 21, the locking fluid bag 22, and the restraining fluid bag 23 attached to the cuff unit 1. In this example, the oscillation circuit 410 oscillates on the basis of an electric signal value based on a change in electric resistance due to the piezoresistive effect from the pressure sensor 41, and outputs a frequency signal having a frequency corresponding to the electric signal value of the pressure sensor 41 to the CPU 100.

In the case of measuring blood pressure according to a general oscillometric method, the following operation is generally performed. That is, the wrist 90 of the subject is put in the cuff unit 1, and upon measurement, the pressurizing pumps 32, 42, the exhaust valves 33, 43, and the 3-port valve 44 are controlled to increase the cuff pressure to be higher than the maximal blood pressure. In this example, in this pressure increasing process, the cuff pressure is detected by the pressure sensor 31, and fluctuation of the arterial volume generated in the artery of the wrist 90 is extracted as a pulse wave signal. On the basis of changes in the amplitude of the pulse wave signal (mainly rising and falling) due to changes in cuff pressure at that time, maximal blood pressure (systolic blood pressure) and minimal blood pressure (astolic blood pressure) are calculated.

(Operation Sequence of Sphygmomanometer)

FIGS. 5A to 5C illustrate a P1 on/off signal, a P2 on/off signal, and a P3 on/off signal, respectively, each indicating a period in which pressure should be applied to the actuator fluid bag 21, the locking fluid bag 22, and the restraining fluid bag 23 in FIG. 1, for blood pressure measurement. FIG. 5D is a diagram illustrating a change in pressure P4 of the pressing fluid bag 24 with passage of time t. The pressure P4 is applied to the pressing fluid bag 24 illustrated in FIG. 1 in order to measure blood pressure. FIGS. 6A to 6G illustrate general operating states of the actuator fluid bag 21, the locking fluid bag 22, the restraining fluid bag 23, the pressing fluid bag 24, and the lock mechanism 18 with passage of time tin FIGS. 5A to 5D.

The CPU 100 stores the P1 on/off signal, the P2 on/off signal, and the P3 on/off signal each indicating a period in which pressure should be applied, and uses the P1 on/off signal, the P2 on/off signal, and the P3 on/off signal for blood pressure measurement operation to be described later.

In the sphygmomanometer 500, the CPU 100 measures the blood pressure value of the subject according to the oscillometric method. Specifically, when the measurement/stop switch 52A is pressed, the sphygmomanometer 500 starts blood pressure measurement.

Before a time point t10 illustrated in FIG. 5, air is not supplied to the actuator fluid bag 21, the locking fluid bag 22, the restraining fluid bag 23, and the pressing fluid bag 24. At this time, as illustrated in FIG. 3, the subject places the wrist 90 on the receiving portions 15, 15' between the restraining fluid bag 23 and the pressing fluid bag 24 of the cuff unit 1. The actuator fluid bag 21 is in a contracted state, and the second wall 12 is on the +X side of the movable range.

Figure 6A:
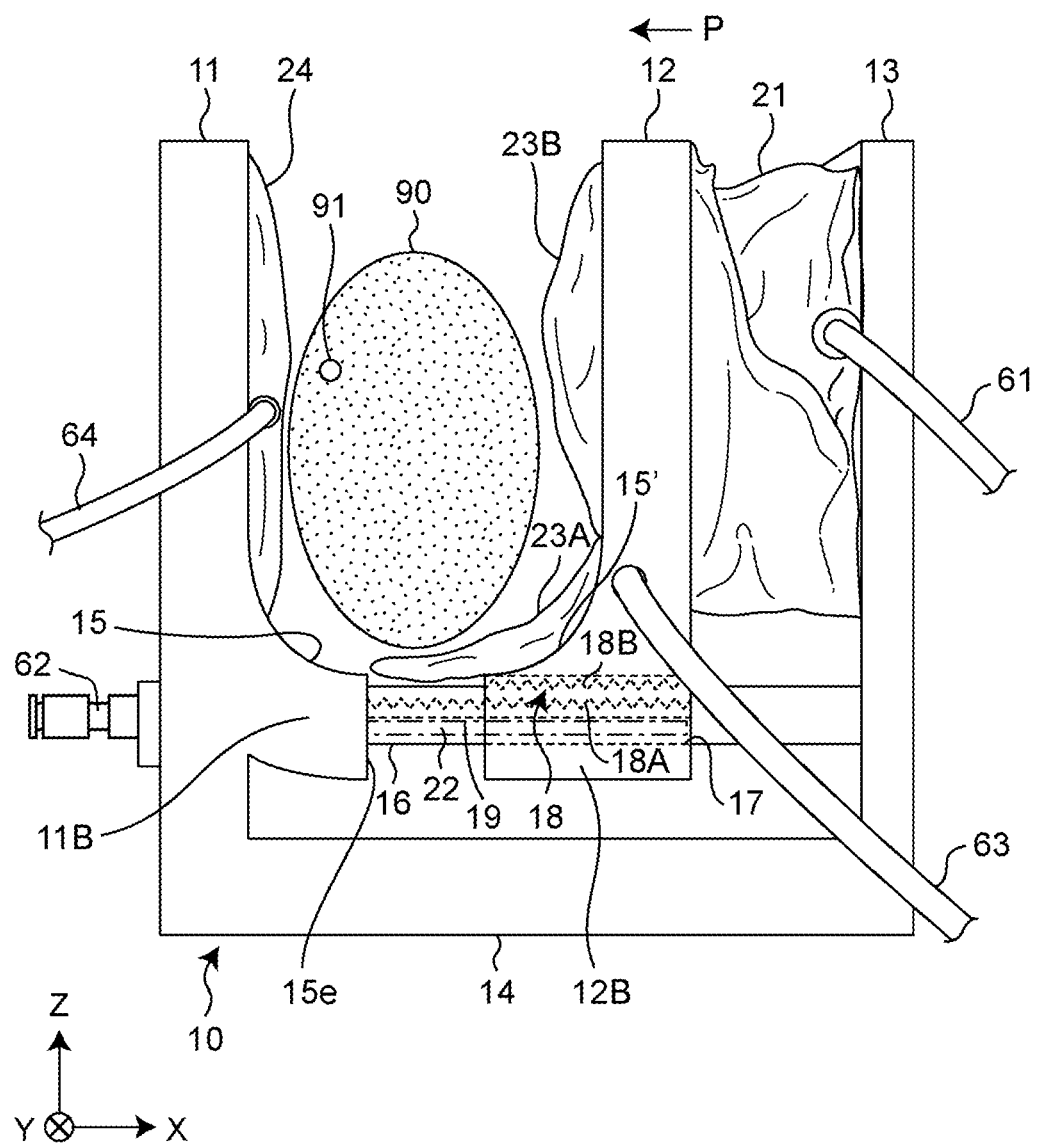
FIG. 6A is a schematic view illustrating operating states of the actuator fluid bag, the locking fluid bag, the restraining fluid bag, and the pressing fluid bag at a time point t10 illustrated in FIGS. 5A to 5D.

Next, at the time point t10 illustrated in FIG. 5, the CPU 100 starts the period indicated by the P1 on/off signal regarding the actuator fluid bag 21, switches the flow path of the 3-port valve 44 through the port switching circuit 450, and supplies air only to the actuator fluid bag 21 until the pressure of the actuator fluid bag 21 reaches a predetermined value (pressure P1). At this time, as illustrated in FIG. 6A, the actuator fluid bag 21 expands and moves the second wall 12 in parallel along the rod members 16 in the −X direction as indicated by an arrow P.

Figure 6B:
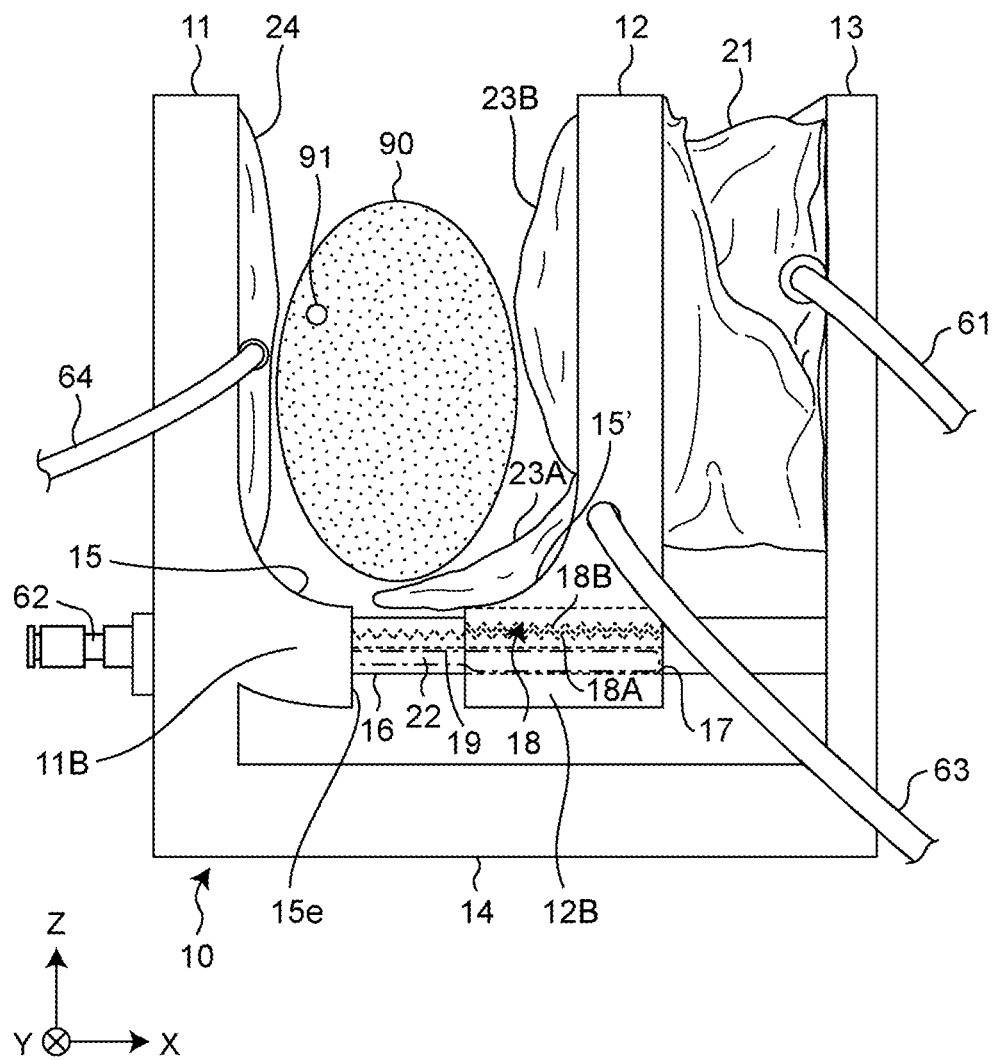
FIG. 6B is a schematic view illustrating operating states of the actuator fluid bag, the locking fluid bag, the restraining fluid bag, the pressing fluid bag, and the lock mechanism at a time point t11 illustrated in FIGS. 5A to 5D.

Next, in a state where air is enclosed in the actuator fluid bag 21 at a time point t11 illustrated in FIG. 5, the CPU 100 switches the flow path of the 3-port valve 44 via the port switching circuit 450 and supplies air to the locking fluid bag 22 until the pressure of the locking fluid bag 22 reaches a predetermined value (pressure P2). From the time point t11, the period indicated by the P2 on/off signal regarding the locking fluid bag 22 starts. At this time, as illustrated in FIG. 6B, the locking fluid bag 22 expands to operate the lock mechanism 18. That is, the first engaging portion 18B and the second engaging portion 18A are engaged with each other, and the second wall 12 is fixed with respect to the first wall 11 in the X direction.

Figure 6C:
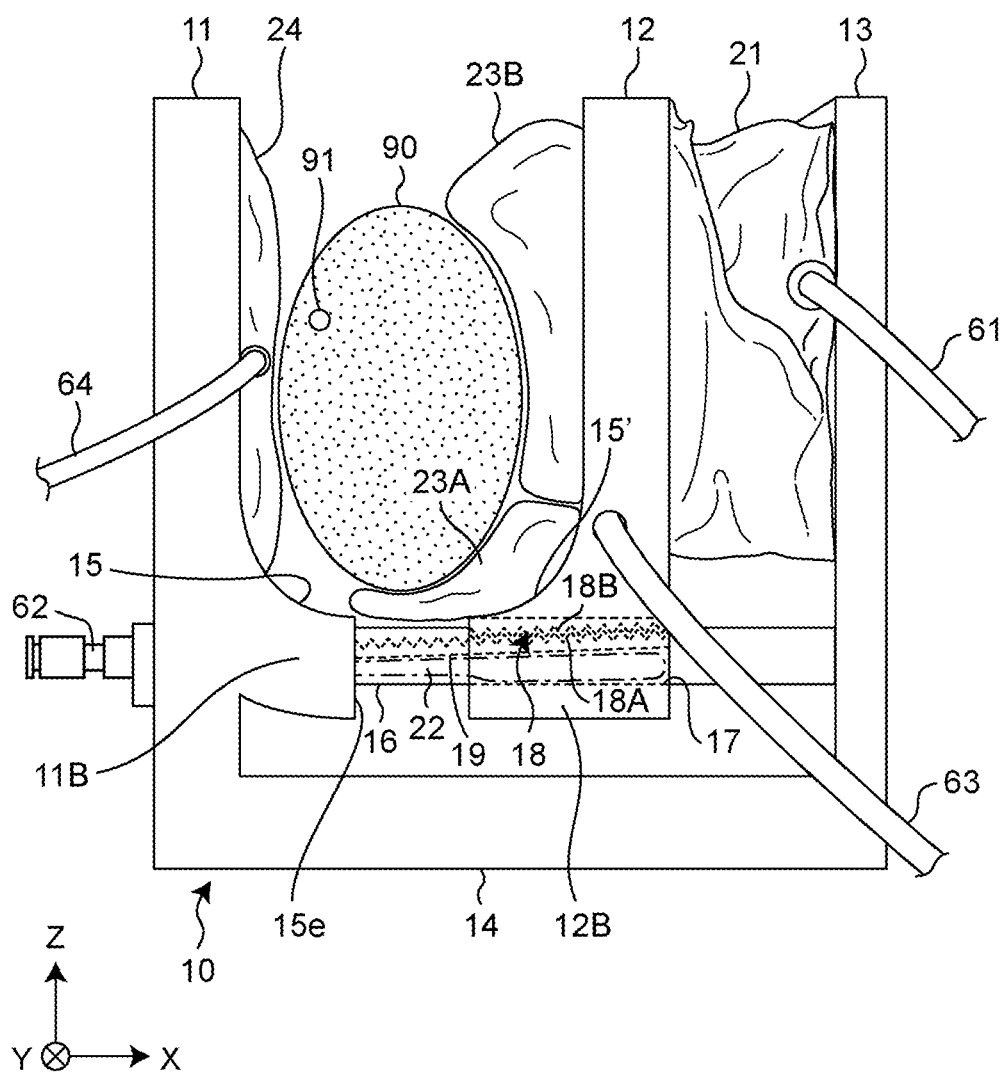
FIG. 6C is a schematic view illustrating operating states of the actuator fluid bag, the locking fluid bag, the restraining fluid bag, the pressing fluid bag, and the lock mechanism at a time point t12 illustrated in FIGS. 5A to 5D.

Next, in a state where air is enclosed in the actuator fluid bag 21 and the locking fluid bag 22 at a time point t12 illustrated in FIG. 5, the CPU 100 switches the flow path of the 3-port valve 44 through the port switching circuit 450, and supplies air to the restraining fluid bag 23 until the pressure of the restraining fluid bag 23 reaches a predetermined value (pressure P3). From the time point t12, the period indicated by the P3 on/off signal regarding the restraining fluid bag 23 starts. At this time, as illustrated in FIG. 6C, the restraining fluid bag 23 expands along the outer periphery of the wrist 90 in a narrow range between the second wall 12 and the first wall 11 that are locked to wrap the wrist 90.

Next, in a state where air is enclosed in the actuator fluid bag 21, the locking fluid bag 22, and the restraining fluid bag 23 at a time point t13 illustrated in FIG. 5, the CPU 100 switches the flow path of the 3-port valve 44 through the port switching circuit 450, and gradually apply pressure P4 to the pressing fluid bag 24 from a pressurization start point A.

As described above, since the first wall 11 and the second wall 12 relatively approach each other with the wrist 90 interposed therebetween, the restraining fluid bag 23 inflates in a relatively narrow range between the second wall 12 and the wrist 90. Further, the pressing fluid bag 24 inflates in a relatively narrow range between the first wall 11 and the wrist 90. Therefore, restraining force and pressing force can be made sufficiently great as the cuff unit 1.

Figure 6D:
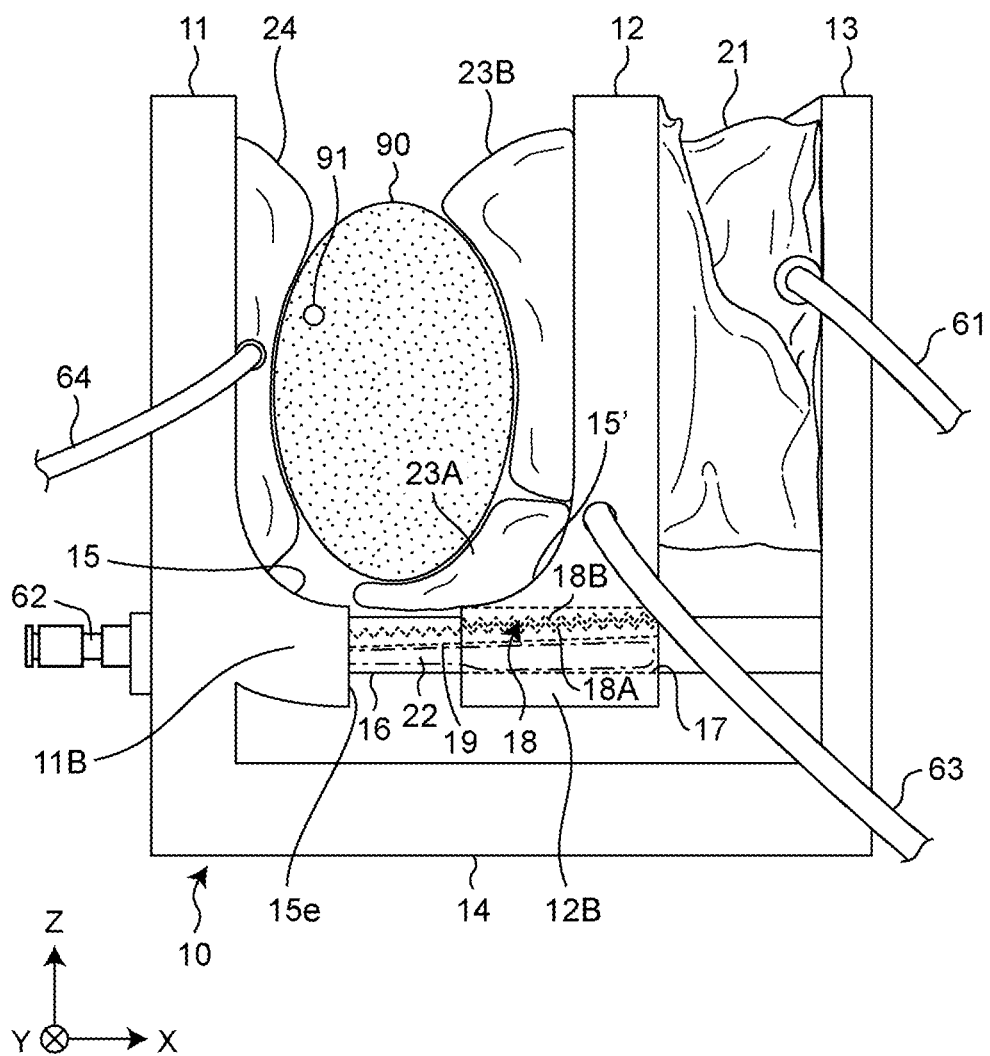
FIG. 6D is a schematic view illustrating operating states of the actuator fluid bag, the locking fluid bag, the restraining fluid bag, the pressing fluid bag, and the lock mechanism at a time point t14 illustrated in FIGS. 5A to 5D.
Figure 6E:
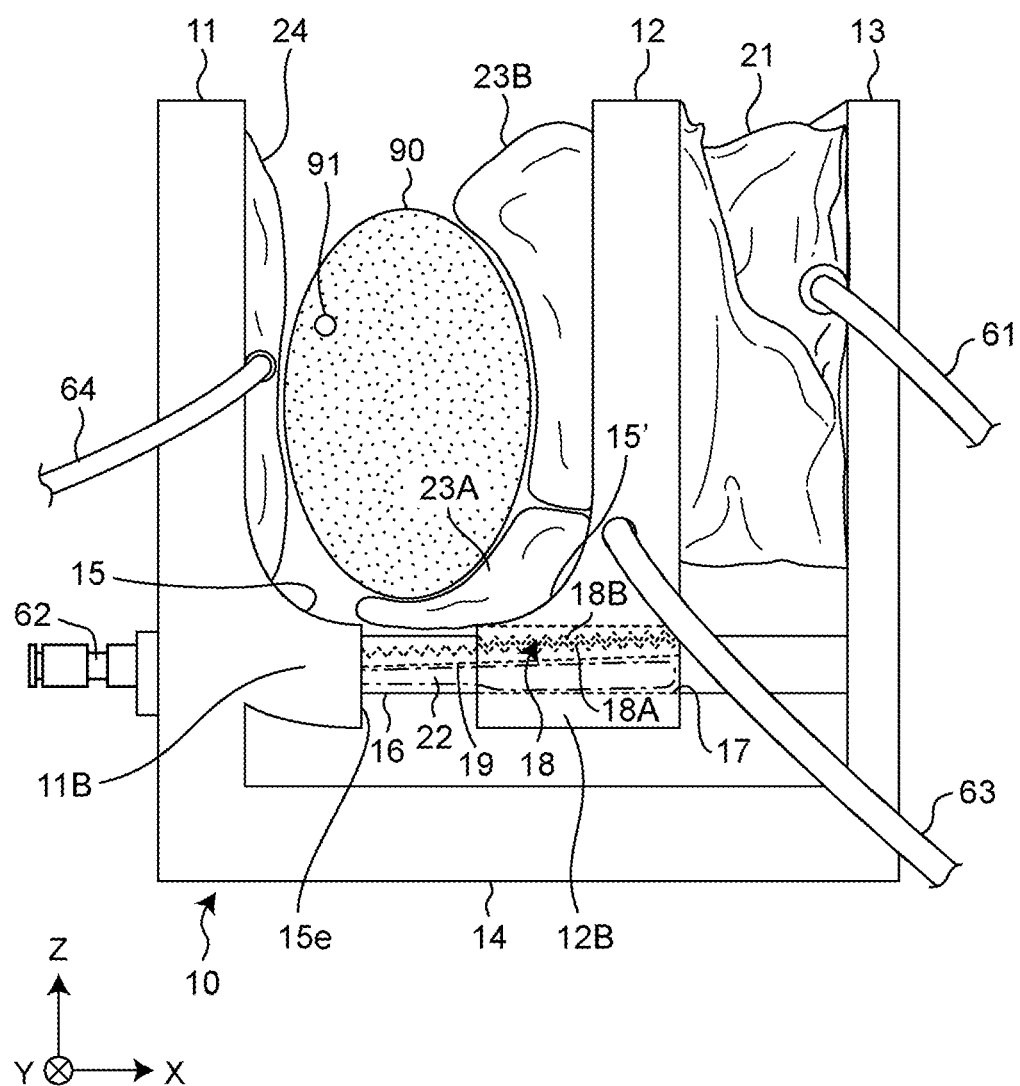
FIG. 6E is a schematic view illustrating operating states of the actuator fluid bag, the locking fluid bag, the restraining fluid bag, the pressing fluid bag, and the lock mechanism at a time point t15 illustrated in FIGS. 5A to 5D.
Figure 6F:
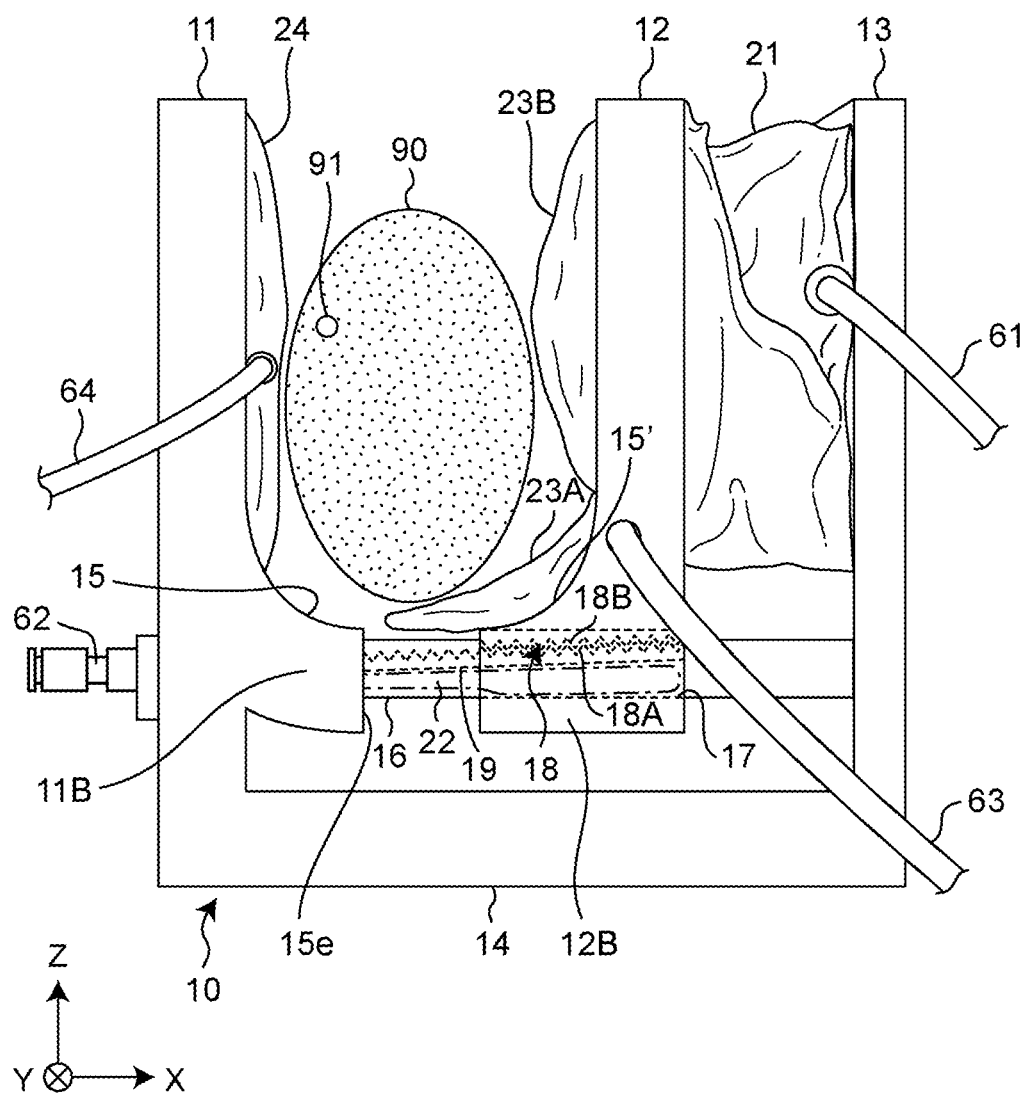
FIG. 6F is a schematic view illustrating operating states of the actuator fluid bag, the locking fluid bag, the restraining fluid bag, the pressing fluid bag, and the lock mechanism at a time point t16 illustrated in FIGS. 5A to 5D.
Figure 6G:
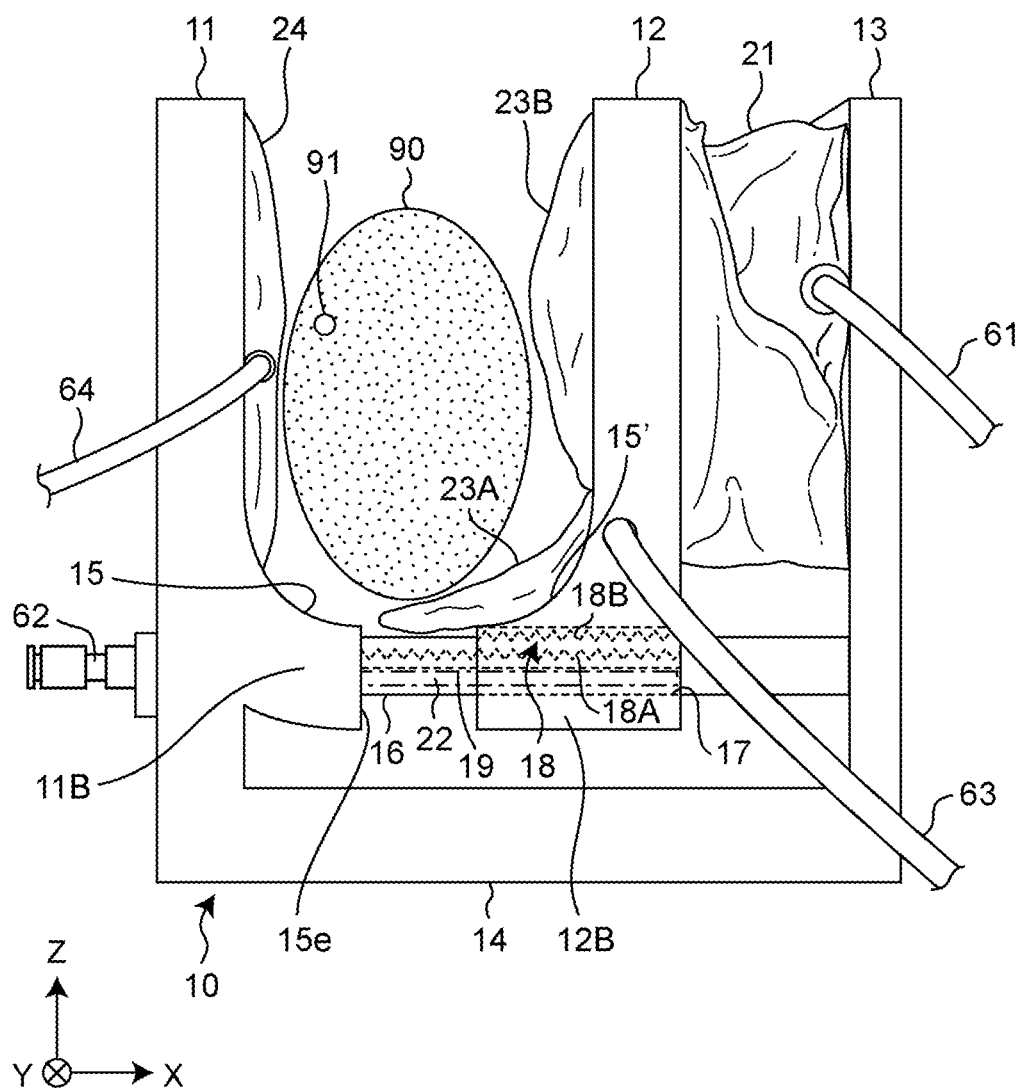
FIG. 6G is a schematic view illustrating operating states of the actuator fluid bag, the locking fluid bag, the restraining fluid bag, the pressing fluid bag, and the lock mechanism at a time point t17 illustrated in FIGS. 5A to 5D.

Next, in this example, before and after a time point t14 in the pressure increasing process, the pressure of the pressing fluid bag 24 is detected by the pressure sensor 31, and fluctuation of the arterial volume generated in the artery of the wrist 90 is extracted as a pulse wave signal. At this time, in the cuff unit 1, as illustrated in FIG. 6D, all the actuator fluid bag 21, the locking fluid bag 22, the restraining fluid bag 23, and the pressing fluid bag 24 are expanded. In the pressure increasing process, the CPU 100 calculates a blood pressure value by applying a known algorithm according to the oscillometric method on the basis of the pulse wave signal. When calculation of the blood pressure value is completed (in this example, it is assumed that calculation of the blood pressure value is completed when the pressure P4 reaches pressure P44) or the measurement/stop switch 52A is pressed, control is performed for stopping the pressurizing pump 42 through the pump drive circuit 420, and then opening the exhaust valve 43 through the valve drive circuit 430. As a result, the pressure P4 is lowered, air is rapidly exhausted from the pressing fluid bag 24, and the pressing fluid bag 24 is contracted. Note that the blood pressure value may not be calculated during the pressure increasing process, but may be calculated during the pressure decreasing process.

The pressures P1 and P3 applied to the actuator fluid bag 21 and the restraining fluid bag 23, respectively, are set to be sufficiently higher than the pressure P44 of the pressing fluid bag 24 that is assumed.

When the blood pressure value is calculated and determined, the CPU 100 performs control for displaying the calculated blood pressure value on the display unit 50 and storing the blood pressure value in the memory 51.

Next, at a time point t15 illustrated in FIG. 5, the CPU 100 performs control for opening the exhaust valve 43 through the valve drive device 430 and switching the exhaust path of the 3-port valve 44 through the port switching circuit 450 to exhaust the air in the restraining fluid bag 23. As a result, the pressure in the restraining fluid bag 23 is reduced, air is rapidly exhausted from the restraining fluid bag 23, and the restraining fluid bag 23 contracts. At the time point t15, the period indicated by the P3 on/off signal regarding the restraining fluid bag 23 ends.

Next, at a time point t16 illustrated in FIG. 5, the exhaust operation of the locking fluid bag 22 is started. The CPU 100 switches the exhaust path of the 3-port valve 44 through the port switching circuit 450 to perform control for discharging the air in the locking fluid bag 22. Thus, the pressure in the locking fluid bag 22 is reduced and the locking fluid bag 22 contracts. As a result, engagement between the first engaging portion 18B and the second engaging portion 18A is released. At the time point t16, the period indicated by the P2 on/off signal regarding the locking fluid bag 22 ends.

Next, at a time point t17 illustrated in FIG. 5, the CPU 100 performs control for switching the exhaust path of the 3-port valve 44 through the port switching circuit 450 to exhaust the air in the actuator fluid bag 21. As a result, the pressure in the actuator fluid bag 21 is lowered and the actuator fluid bag 21 contracts. At the time point t17, the period indicated by the P1 on/off signal regarding the actuator fluid bag 21 ends. Then, the wrist 90 is taken out from the cuff unit 1.

In the above example, all of the first wall 11, the second wall 12, and the third wall 13 of the cuff unit 1 are flat plates; however, the present invention is not limited to this. For example, when viewed from the side as illustrated in FIG. 3, each of the first wall 11, the second wall 12, and the third wall 13 has a plate shape curved in a substantially arc shape so as to be recessed toward the wrist 90.

In the above example, the actuator is configured to be expanded or contracted by the fluid bag; however, is not limited to this. Furthermore, the lock mechanism is also configured to be expanded or contracted by the fluid bag; however, is not limited to this. For example, the actuator and the lock mechanism may have mechanical systems that can expand and contract in the X and Y directions, respectively.

As described above, a cuff unit restraining and pressing an object which has a rod shape, the cuff unit of the present disclosure comprises:
a first wall and a second wall that face each other with the object which has the rod shape interposed therebetween;
an actuator that is capable of moving the first wall and the second wall in parallel with each other in a direction in which the first wall and the second wall relatively approach each other or separate from each other;
a pressing fluid bag that is provided on a surface of the first wall on a side facing the object and that receives supply of a fluid from outside to inflate and press the object;
a restraining fluid bag that is provided on a surface of the second wall on a side facing the object and that receives supply of a fluid from outside to inflate along a periphery of the object;
a third wall that is disposed to face a surface of the second wall on a side opposite to the first wall;
a support wall that integrally connects sides of the first wall and the third wall which face each other; and
an actuator fluid bag that is provided between the second wall and the third wall and that receives supply of a fluid from outside to expand,
wherein the actuator expands or contracts the actuator fluid bag when the actuator moves the first wall and the second wall in parallel with each other in the direction in which the first wall and the second wall relatively approach each other or separate from each other.

In the present description, the term "object which has a rod shape" typically refers to a portion to be measured such as an upper limb (wrist, upper arm, or the like) or a lower limb (ankle or the like); however, is not limited to part of a living body. The object may also be an inanimate object.

In addition, the term "outside" in the phrase, a pressing fluid bag "receives supply of a fluid from outside", means outside of the pressing fluid bag. Similarly, the term "outside" in the phrase, a restraining fluid bag "receives supply of a fluid from outside", means outside of the restraining fluid bag. Similarly, the term "outside" in the phrase, an actuator fluid bag to be described later "receives supply of a fluid from outside", means outside of the actuator fluid bag.

In the cuff unit according to the present disclosure, the object which has the rod shape is provided between the first wall and the second wall, and the first wall and the second wall face each other with the object interposed therebetween. The actuator moves the first wall and the second wall in parallel with each other in a direction in which the first wall and the second wall relatively approach each other. The restraining fluid bag receives supply of a fluid from outside to inflate, and extends along the periphery of the object from a surface of the second wall on a side facing the object. The pressing fluid bag receives supply of a fluid from outside to inflate, and presses the object from a surface of the first wall on a side facing the object. Here, since the first wall and the second wall relatively approach each other with the object interposed therebetween, the restraining fluid bag inflates in a relatively narrow range between the second wall and the object. Further, the pressing fluid bag inflates in a relatively narrow range between the first wall and the object. Therefore, restraining force and pressing force can be made sufficiently great as the cuff unit. Note that when the object is removed from the cuff unit, the fluid is discharged from the pressing fluid bag and the restraining fluid bag, and the actuator allows the first wall and the second wall to move in parallel with each other in a direction in which the first wall and the second wall relatively separate from each other. As a result, it is possible to remove the object from the cuff unit. In addition, expansion or contraction of the actuator fluid bag can be performed according to control similar to control of expansion or contraction of the pressing fluid bag and the restraining fluid bag. Therefore, the control system of this cuff unit is simplified. In addition, when a user feels an abnormality during use by any chance, it is possible to easily remove the object from the cuff unit by deforming the actuator fluid bag.

In the cuff unit of one embodiment, the cuff unit comprises a rod member that extends from part of the first wall toward the second wall in a direction perpendicular to the first wall, wherein the actuator moves the second wall in parallel along the rod member.

In the cuff unit according to this embodiment, the first wall and the second wall can be relatively stably moved in parallel with each other.

In the cuff unit of one embodiment, the cuff unit comprises a lock mechanism that is capable of fixing a relative position of the second wall with respect to the first wall in a direction in which the first wall and the second wall move in parallel with each other.

In the cuff unit of this embodiment, in a state where, regarding the direction in which the first wall and the second wall move in parallel with each other, the lock mechanism fixes the relative position of the second wall with respect to the first wall, the second wall does not move away from the first wall when the restraining fluid bag and the pressing fluid bag expand. Therefore, the restraining force and the pressing force can be made further greater as the cuff unit.

In the cuff unit of one embodiment, the second wall has a through hole that penetrates the second wall in the direction in which the first wall and the second wall move in parallel with each other, and the lock mechanism includes an uneven first engaging portion that is formed on an edge portion of the through hole of the second wall, and a plate member that is disposed to face the edge portion of the through hole of the second wall and whose position with respect to the first wall in the direction in which the first wall and the second wall move in parallel with each other is fixed, the plate member having an uneven second engaging portion that is disposed on a surface facing the edge portion of the through hole of the second wall, and a locking fluid bag that receives supply of a fluid from outside to expand and urges the plate member toward the edge portion of the second wall such that the second engaging portion meshes with the first engaging portion.

In the cuff unit according to this embodiment, a locking fluid bag that constitutes the locking mechanism receives supply of a fluid from outside to expand, and urges the plate member toward the edge portion of the second wall. Therefore, the uneven first engaging portion meshes with the uneven second engaging portion. As a result, regarding the direction in which the first wall and the second wall move in parallel with each other, the second wall is locked with respect to the first wall. Note that when the object is removed from the cuff unit, the fluid is discharged from the locking fluid bag, and then the uneven first engaging portion and the uneven second engaging portion are disengaged. As a result, it is possible to remove the object from the cuff unit. Moreover, expansion or contraction of the locking fluid bag can be performed according to control similar to control of expansion or contraction of the pressing fluid bag and the restraining fluid bag. Therefore, the control system of this cuff unit is simplified.

In another aspect, a sphygmomanometer of the present disclosure comprises:

the cuff unit; and a pressure sensor that detects pressure of the pressing fluid bag.

Here, in the sphygmomanometer according to the present disclosure, since the first wall and the second wall relatively approach each other with the object interposed therebetween, the restraining fluid bag inflates in a relatively narrow range between the second wall and the object. Furthermore, the pressing fluid bag inflates in a relatively narrow range between the first wall and the object. Therefore, restraining force and pressing force can be made sufficiently great as the cuff unit. As a result, blood pressure can be measured on the basis of output from the pressure sensor.

The above embodiments are illustrative, and various modifications can be made without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A cuff unit configured to restrain and press an object that has a rod shape, the cuff unit comprising:
   a first wall and a second wall that each have a flat plate shape, are separated from and face to each other, and are arranged to receive the object having the rod shape between the first wall and the second wall when the cuff unit is used, the second wall being translationally movable in a first direction in which the second wall relatively approaches to the first wall or separates from the first wall;
   a pressing fluid bag that is provided on a surface of the first wall on a side facing the object and that receives supply of a fluid from outside to inflate and press the object;
   a restraining fluid bag that is provided on a surface of the second wall on a side facing the object and that receives supply of a fluid from outside to inflate along a periphery of the object;
   a third wall that has a flat plate shape, is separated from and faces a surface of the second wall on a side opposite to the first wall;
   a support wall that extends in the first direction in a manner separated from the second wall and integrally connects sides of the first wall and the third wall which face to each other, the first wall, the third wall and the support wall constituting an integral outer frame of the cuff unit; and
   an actuator fluid bag that is provided between the second wall and the third wall and that receives supply of a fluid from outside to expand; and
   a pressurizing pump that supplies the fluid to the actuator fluid bag to expand, and an exhaust valve that discharges the fluid from the actuator fluid bag to contract, such that the second wall moves translationally in the first direction between the first wall and the third wall.

2. The cuff unit according to claim 1, further comprising a rod member that extends from part of the first wall toward the second wall in the first direction perpendicular to the first wall,
   wherein the actuator fluid bag expands or contracts to move the second wall translationally along the rod member.

3. The cuff unit according to claim 1, further comprising a lock mechanism that is capable of fixing a relative position of the second wall with respect to the first wall in the first direction.

4. The cuff unit according to claim 3, wherein
   the second wall has a through hole that penetrates the second wall in the first direction, and
   the lock mechanism includes
      an uneven first engaging portion that is formed on an edge portion of the through hole of the second wall, and
      a plate member that is disposed to face the edge portion of the through hole of the second wall and whose position with respect to the first wall in the first direction is fixed, the plate member having an uneven second engaging portion that is disposed on a surface facing the edge portion of the through hole of the second wall, and
      a locking fluid bag that receives supply of a fluid from outside to expand and urges the plate member toward the edge portion of the second wall such that the second engaging portion meshes with the first engaging portion.

5. A sphygmomanometer comprising:
   the cuff unit according to claim 1; and
   a pressure sensor that detects pressure of the pressing fluid bag.

* * * * *